United States Patent [19]
Romaschin et al.

[11] Patent Number: 6,159,683
[45] Date of Patent: *Dec. 12, 2000

[54] METHOD OF DETERMINING STAGE OF SEPSIS

[75] Inventors: Alexander D. Romaschin, Etobicoke; Paul M. Walker, Toronto, both of Canada

[73] Assignee: Spectral Diagnostics, Inc., Toronto, Canada

[ * ] Notice: This patent is subject to a terminal disclaimer.

[21] Appl. No.: 08/991,109

[22] Filed: Dec. 16, 1997

[51] Int. Cl.[7] .............................. C12Q 1/70; C12Q 1/10; G01N 33/53; G01N 33/563
[52] U.S. Cl. .................................. 435/5; 435/6; 435/7.1; 435/7.2; 435/7.24; 435/7.31; 435/7.37; 435/25; 435/34; 435/38; 435/962; 435/968; 435/973; 435/975; 436/513; 436/578; 436/536; 436/539; 436/808; 436/811
[58] Field of Search .............................. 435/5, 6, 7.1, 7.2, 435/7.24, 7.31–7.37, 25, 34, 38, 962, 968, 973, 975; 436/513, 578, 536, 539, 808, 811

[56] References Cited

U.S. PATENT DOCUMENTS

| | | |
|---|---|---|
| 4,647,532 | 3/1987 | Watanabe et al. . |
| 4,737,455 | 4/1988 | De Baetselier . |
| 4,959,302 | 9/1990 | Cornaby et al. . |
| 5,108,899 | 4/1992 | Allen . |
| 5,210,019 | 5/1993 | Margalit . |
| 5,294,541 | 3/1994 | Kaplan et al. . |
| 5,804,370 | 9/1998 | Romaschin et al. . |

FOREIGN PATENT DOCUMENTS

| | | |
|---|---|---|
| 0430440 | 10/1990 | European Pat. Off. . |
| 2131948 | 5/1983 | United Kingdom . |
| WO 90/06514 | 6/1990 | WIPO . |
| WO 92/03734 | 3/1992 | WIPO . |
| WO 92/16553 | 10/1992 | WIPO . |
| WO 94/29728 | 12/1994 | WIPO . |

OTHER PUBLICATIONS

Lilius et al. (1992) J. Biolumines. Chemilumines. 7:117–22.
Michie (1992) Proc. Brussels Symp., pp. 329–338.
Romaschin et al. (1996) Clin. Chem. 42:S130 (No. 146).
Winkelhake et al. (1992) J. Infect. Dis. 165:26–33.
Ziegler et al. (1991) New England J. Medicine 324(7):429–36.
Zeller et al. (1992) New England J. Medicine 52:449–55.

*Primary Examiner*—Nita Minnifield
*Assistant Examiner*—Padma Baskar
*Attorney, Agent, or Firm*—Klauber & Jackson

[57] ABSTRACT

The invention relates to a method for staging sepsis in a patient by concurrently measuring in a sample of the patient's blood four parameters which are indicative of the stage of sepsis: 1) the level of microbial product level in the blood; 2) the level of tumor necrosis factor (TNF) response reserve; 3) the maximum oxidant production by neutrophils, and 4) the responsiveness of the patient's neutrophils to immunocomplexes. Based on determining the stage of sepsis, appropriate treatment for the patient may be identified.

11 Claims, 3 Drawing Sheets

FIG. 3A

× pau11193/25+26+27
□ pau11193/28+29+30

FIG. 3B

× dav23042/19+20+21
□ dav23042/22+23+24

METHOD OF DETERMINING STAGE OF SEPSIS

FIELD OF THE INVENTION

This invention relates to methods to determine the stage of sepsis in a patient. The method comprises measurement of the following blood analytes or white blood cell functions: 1) the level of microbial product level in the blood; 2) the tumor necrosis factor (TNF) response reserve of neutrophils; 3) the maximum oxidant production by neutrophils, and 4) the responsiveness of the patient's neutrophils to immunocomplexes. Based on determining the stage of sepsis, appropriate treatment for the patient may be identified.

DEFINITIONS

"Sepsis" is defined as a pathological condition of the body resulting from the presence of infectious microorganisms, which clinically manifests as one or more of the following sequelae: pyrexia, hypotension, hypoxemia, tachycardia, hypothermia, neutrophilia, and neutropenia.

"Antigen" as used in the context of the method of the present invention refers specifically to a material which reacts with a complementary antibody and which in the presence of white blood cells maximally stimulates the production of oxidants. This antigen may or may not be the same as the microbial product being measured in the assay.

"Immunocomplex" is a synonym for an antibody-antigen complex.

"Opsonized" refers to a particle to which immunoglobulin and complement factors are bound and which results in a more vigorous recognition of the particle by the immune system. For example, the yeast polysaccharide zymosan, or latex particles, such as polystyrene, may be opsonized by binding of immunoglobulin and complement factors to their surfaces; opsonized zymosan or latex will stimulate increased oxidant production by white cells after they are activated by exposure to immunocomplexes.

"Responsiveness" is an indication of the immunocompetence of the patient's white blood cells, i.e., the maximum extent to which the neutrophils respond to immunocomplexes. It is measured by maximally stimulating the patient's white blood cells with immunocomplexes, versus a control of stimulation with antigen only, and represents the remaining white cell oxidative capacity in cells naive to exposure to a maximum stimulatory dose of immunocomplexes. Responsiveness is expressed as 1-[(light integral from exposure to maximal antigen alone)/(light integral from exposure to maximal immunocomplexes)].

"Maximum chemiluminescence (CLmax)" is a measure of the maximum oxidant production by a sample of neutrophils when stimulated by a non-rate-limiting concentration of phagocytic stimulus.

"Tumor necrosis factor (TNF) response reserve" is a measure of the ability of neutrophils to be further primed by a maximum stimulatory dose of TNF.

BACKGROUND OF THE INVENTION

Sepsis is a serious and potentially lethal pathological condition of the body resulting from the presence of infectious microorganisms. This condition clinically manifests as one or more of the following sequelae: pyrexia (fever), hypotension (low blood pressure), hypoxemia (low blood oxygen tension), tachycardia (elevated heart rate), hypothermia (decreased body temperature), neutrophilia (increased numbers of circulating neutrophils), and neutropenia (decreased numbers of circulating neutrophils). While these sequelae individually may have profound effects on normal body physiology, in excess or in combination they lead to an acute pathological state called shock, which is often fatal if not treated rapidly and aggressively. For example, hospital and particularly intensive care unit patients who have acquired nosocomial infections as a result of peri- or post-operative immunosuppression or secondary to other disease processes, such as pancreatitis, hypotensive or hypovolemic shock, physical trauma, burn injury, or organ transplantation, and develop septic shock syndrome have a mortality which has been quoted to range from 30–70% depending upon other co-incident complications.

Treatment of sepsis patients is not straightforward. Depending on the specific stage of sepsis and the corresponding status of the patient's immune system, a particular treatment may be ineffective or even exacerbate the patient's condition. Early in sepsis, when circulating microorganisms are present, the most appropriate treatment is that directed specifically against microorganisms and microbial products, such as antibiotic or anti-microbial toxin therapies, including anti-lipopolysaccharide (LPS) antibodies, polymyxin derivatives, and synthetic HDL. At this stage, the patent's immune system is only slightly compromised. Once the level of microorganisms and their toxic products has increased, microbial cell products stimulate the body's white blood cells to secrete inflammatory mediators, such as tumor necrosis factor (TNF) and interleukin-1 (IL-1), which are responsible for many of the early sequelae and symptoms of sepsis. At this stage, antibiotic and anti-microbial therapies are less effective, and the patients should be treated with agents to inactivate inflammatory mediators, such as anti-cytokine antibodies, interleukin receptor antagonists, TNF receptor, pentoxyphylline, or anti-inflammatory cytokines such as interleukin-11 (IL-11). At this stage the patient's immune system is in a hyperactivated state. Further progression of sepsis leads to a severe decline in the immune responsiveness of the patient, a condition called anergy, in which the immune system fails. The patients white blood cells are increasingly unable to destroy microorganisms. At this stage, both of the aforementioned therapies are mostly ineffective and the patient must be treated with immune system stimulants, such as glutamine, non-steroidal anti-inflammatory agents, granulocyte colony stimulating factor, betafectin, and interleukin-11 (IL-11) in order to rescue the patient from impending demise. Thus, without knowing the stage of sepsis, appropriate treatments may be ineffective or withheld, contributing to the eventual demise of the patient.

Furthermore, despite the development of increasingly potent antimicrobial agents, the incidence of nosocomial infections and in particular, infections leading to sepsis or septicemia, is increasing. The difficulty with many of the promising therapeutic agents is that their window of opportunity and indications for use have not been adequately delineated largely due to a lack of appropriate rapid and quantitative diagnostic procedures and partly due to a lack of complete understanding of the pathogenesis of the sepsis syndrome. For example, until the recent advent of novel therapeutic strategies, sepsis patients have been managed largely by palliative care and administration of antibiotics. The biotechnology industry has facilitated the large scale production of many new targeted biopharmaceuticals which utilize monoclonal antibodies against such initiators of sepsis as gram-negative endotoxin (Centocor's HA-1 A(R) or Xoma's Xomen-E5(R)), tumor necrosis factor (various producers including Hoffman La Roche and Centocor with patents WO 90/06514 and WO 92/16553), interleukins, as well as various soluble receptor antagonists such as IL-1 RA (Synergen) and $sCR_1$ (soluble complement receptor 1)—a truncated recombinant complement regulatory molecule. The cost of these therapeutic agents is significant, being priced at $3,000.00 to $4,000.00 per dose. Thus, providing this therapy indiscriminately to patients would add a considerable burden to the health care system without providing a corresponding benefit to patients.

Notably absent from the physician's diagnostic armamentarium is a method and diagnostic test to easily and rapidly determine the patient's stage of sepsis at a specific time, so that the appropriate therapy may be initiated. Staging sepsis requires knowledge of several factors, including the level of microbial products in the patient's blood and the status of the patient's white blood cells. Presently these assessments may be made utilizing several diverse methods and test procedures. Centocor Inc.'s immunometric assay for tumor necrosis factor-alpha (TNF-$\alpha$), as described in WO 90/06314, uses two antibodies, one of which is labeled, to measure the level of this inflammatory mediator. The National Aeronautics and Space Administration detects Pseudomonas bacteria by extraction of Azurin and detection using Azurin-specific antibody (U.S. Pat. No. 5,210,019). The endotoxin assay kit from BioWhittaker (Walkerville, Md., U.S.A.) or Seikagaku Kogyo Ltd. (Tokyo, Japan) is a Limulus Amebocyte Lysate (LAL) Assay technique also measure levels of endotoxin. Stevens et al. (J. Infect. Disease 170:1463–1472, 1994) provide a complex automated method for determining phagocyte function utilizing several measures: phorbol myristate acetate (PMA)-stimulated oxidase activity, PMA-stimulated simple dioxygenation, and circulating and primed opsonin receptor-dependent dioxygenation activity. These data provide a measure of the state of circulating phagocytes, which represents incomplete information for determining the stage of sepsis of the patient.

Copending application Ser. No. 08/552,145 now U.S. Pat. No. 5,804,370 and Ser. No. 08/516,204 now abonded, incorporated herein by reference, describe methods that may be used to indicate the presence of microbial products in a patient's blood sample by first forming an immunocomplex between the preselected microbial product and an antibody thereto which is added to the sample. Any immunocomplex formed as a result then activates complement present in the blood sample which in turn causes neutrophils and other white blood cells present in the blood sample to produce oxidants. The oxidants then cause an added chemiluminogenic compound, such as luminol, to release light energy. The white blood cells optionally may be stimulated through the addition of opsonized zymosan or other agents resulting in increased production of oxidants. The amount of light emitted over time may be measured by a luminometer device to indicate the presence of the microbial product in the sample. A control sample without the addition of antibody is included, to which is also added any additional stimulatory agents. This method provides a semi-quantitative determination of the level of the pre-selected microbial product in the blood sample.

Copending and concurrently filed application Ser. No. 08/991,230, incorporated herein by reference, is an improvement of the aforementioned applications in that an analyte such as endotoxin or other microbial product present in a patient's blood sample may be quantitated by combining the procedure described in the aforementioned applications with a measurement of the maximum response of the patient's white blood cells to a maximum stimulatory level of immunocomplexes. Because the level of analyte in the sample is directly related to the ratio of the chemiluminescent response from the analyte-formed immunocomplexes to the chemiluminescent response to a maximum stimulatory dose of immunocomplexes, the analyte may be quantitated in a patient's sample containing analyte and white blood cells.

It has now been found that the stage of sepsis in a patient may be determined rapidly and accurately from a sample of blood by determining microbial product levels in the sample, concurrently with an assessment of several white blood cell functions.

BRIEF DESCRIPTION OF THE INVENTION

This invention provides a method for determining the stage of sepsis in a patient by concurrently measuring in a sample of blood the following parameters: (i) the level of microbial products; (ii) the TNF response reserve or the ability of neutrophils to be further primed by a maximum stimulatory dose of TNF; (iii) the maximum oxidant production by the patient's white blood cells; and (iv) the level of responsiveness of the patient's white blood cells to a maximum stimulatory level of immunocomplexes.

The microbial products indicative of sepsis include gram-positive bacteria, gram-negative bacteria, fungi, viruses, gram-positive cell wall constituents such as lipoteichoic acid, peptidoglycan and teichoic acid, gram-negative endotoxin, and lipid A.

In one embodiment, the assessment of the four parameters may be carried out by the following sequential steps. (1) Five aliquots of equal volume of the blood sample, indicated as aliquots A. B, C, D and E, are provided. (2) Aliquot B is combined with an amount of anti-microbial product antibody sufficient to form an immunocomplex with the microbial product in the sample; this aliquot hereafter referred to as reaction aliquot B. (3) Aliquot A is used as a control to reaction aliquot B without said anti-microbial product antibody; this aliquot is hereafter referred to as reaction aliquot A. (4) Aliquot D is combined with a maximal stimulatory amount of antigen, together with an amount of anti-antigen antibody sufficient to form an immunocomplex with the anti-antigen antibody; this aliquot hereafter referred to as reaction aliquot D. (5) Aliquot C is provided as a control to reaction aliquot D, containing an amount of antigen equal to that provided in reaction aliquot D, but without said anti-antigen antibody; this aliquot is referred to as reaction aliquot C. (6) Aliquot E is combined with a maximum stimulating dose of tumor necrosis factor; this aliquot is referred to as reaction aliquot E. (7) Reaction aliquots A, B, C, D and E are incubated for a time sufficient for any immunocomplexes present or formed in reaction aliquots A, B, C, or D to react with the white blood cells and complement proteins in the plasma to produce oxidants, and for the tumor necrosis factor in reaction aliquot E to maximally prime white blood cells to produce oxidants. (8) An agent capable of stimulating oxidant production by white blood cells on exposure to immunocomplexes or tumor necrosis factor, and a chemiluminescent compound which reacts with said oxidants to generate light, is added to reaction aliquots A, B, C, D, and E, prior to or after the previous step. (9) Light emission is measured from reaction aliquots A, B, C, D and E over a predetermined time period, and by correlating differences in light emission among reaction aliquots A, B, C, D and E, the patient's stage of sepsis is identified.

Typical agents capable of increasing oxidant production by white blood cells on exposure to immunocomplexes or tumor necrosis factor include zymosan, latex particles, opsonized zymosan, or opsonized latex particles; opsonized zymosan is preferred. Examples of useful chemiluminescent compounds which may be employed in the present invention include luminol, lucigenin and pholasin; luminol is preferred.

The antibody and antigen are preferably anti-lipopolysaccharide (anti-endotoxin) antibodies and lipopolysaccharide (endotoxin), respectively. The anti-microbial product antibody is preferably a monoclonal antibody of class IgM or IgG.

A further aspect of the present invention is to provide a diagnostic kit for determining the stage of sepsis from a sample of patient's blood. The kit comprises a first container of IgM or IgG antibody specific to a microbial product, a second container of chemiluminescent compound, a third container of antigen, a fourth container of anti-antigen antibodies, a fifth container of tumor necrosis factor, and a sixth container of an agent capable of increasing oxidant production by white blood cells on exposure to immuno-complexes or tumor necrosis factor.

A wide variety of microbial products may be assessed with the diagnostic kit. These include for example gram-positive bacteria, gram-negative bacteria, fungi, viruses, gram-positive cell wall constituents such as lipoteichoic acid, peptidoglycan and teichoic acid, gram-negative endotoxin, and lipid A. In a preferred embodiment, the diagnostic kit includes an additional container containing an agent capable of increasing oxidant production by white blood cells on exposure to immunocomplexes, for example, zymosan, latex particles, opsonized zymosan, or opsonized latex particles. Opsonized zymosan is preferred.

It is a further objective of the present invention to provide a method for rapidly and accurately determining the stage of sepsis in a patient so that effective and appropriate therapy may be initiated to avert the lethal consequences of sepsis.

BRIEF DESCRIPTION OF THE DRAWINGS

Preferred embodiments of the invention are demonstrated with respect to the drawings wherein.

DETAILED DESCRIPTION OF THE INVENTION

This invention provides a method for accurately identifying the stage of sepsis of a patient. As sepsis is a severe and often rapidly fatal complication arising from the presence of microorganisms in circulation, knowledge of the stage of sepsis is important for choosing the most appropriate therapy, as the wrong therapy may not only be ineffective but may exacerbate the patient's worsening condition. Sepsis patients progress from an early stage (the "early infection" stage) in which microorganisms and their toxic products are present in circulation and the immune system is slightly depressed, to a second stage (the "cytokinemic" stage) in which inflammatory mediators produced by the patient's white blood cells in response to the microbial products cause adverse effects on multiple body systems. At this stage, the patient's immune system is in a hyperactivated state. Without treatment, patients in the cytokinemic stage progress to a third stage (the "anergic" stage) in which the patient's white blood cell function becomes progressively inactivated. In this final stage of anergy, during the terminal stage of the condition, the patient's immune system is progressively weakening in its ability to combat microbial infection. Patients progressing to this latter stage suffer a very poor prognosis.

The present invention uses a combination of four assessments on a patient's blood sample to provide information necessary to determine a patient's stage of sepsis. These assessments are described in detail below.

I. Circulating microbial product level. The presence of microorganisms and mircrobial products in the blood initiates sepsis. For example, early in gram-negative sepsis, endotoxin (LPS) may be present in circulation at between about 50 and about 400 pg/ml. During the cytokinemic stage, levels may be from about 50 to greater than 800 pg/ml. During the anergic stage, levels may be greater than 800 pg/ml. Therapies directed against microorganisms (antibiotics) and their products (anti-LPS antibodies, polymyxin, and synthetic HDL among others) are maximally effective during the early infection phase; beyond this stage, they are less effective or ineffective.

Measurement of circulating microbial products may be achieved by any of several methods, several of which have been described by way of background, above. As a preferred procedure, the method described in co-pending and concurrently filed application Ser. No. 08/991,230, herein incorporated by reference, provides a quantitative determination of the level of an analyte, in this case a microbial product, in a patient's blood sample. As will be seen below, the use of this preferred method also provides the basis for the other concurrent assessments contemplated in the present invention.

The preferred quantitative assessment method for microbial product levels in a patient's sample utilizes the patient's own white blood cells as a mechanism to convert microbial product level into an assay read-out. The method is based upon (1) the specificity of antigen-antibody interactions, i.e., the formation of immunocomplexes between the microbial product present in the sample and exogenously-added anti-microbial product antibodies; (2) the production of oxidants by white blood cells upon exposure to immunocomplexes and relevant complement protein present in blood, the level of oxidant production proportional to the level of immunocomplexes, and thus the amount of microbial product in the sample; and (3) the high sensitivity of chemiluminescent light emission in response to oxidant production by white blood cells in the presence of certain chemiluminescent agents. To practice the method a blood sample is obtained, and divided into four aliquots. Two of the four aliquots are used to assess the chemiluminescent response of the white blood cells in the sample to immunocomplexes formed from the binding of any microbial product present in the sample with an antibody or antibodies to the microbial product which are added to the aliquot, the other aliquot used as a control. The second two aliquots are used to assess the overall maximum response of the white blood cells in the sample to maximal stimulation by immunocomplexes, by adding a large amount of an antigen and its corresponding antibody to one of the aliquots, and only the antigen to the other aliquot as the control. Furthermore, a compound capable of producing light in response to the production of oxidants by white blood cells is added to all aliquots, and also an agent to generally enhance the chemiluminescent response, are added to all of the aliquots. Light emission from all four reaction aliquots is measured over a period of time. The amount of light produced by each aliquot is used to calculate the quantity of preselected analyte in the blood sample, based on a preestablished correlation between the amount of preselected analyte in the sample and the ratio between the integrated chemiluminescence of the four samples described above.

The microbial product analyte may be selected from any of a number of such products, including gram-positive bacteria, gram-negative bacteria, fungi, viruses, gram-positive cell wall constituents such as lipoteichoic acid, peptidoglycan and teichoic acid, gram-negative endotoxin, and lipid A.

The individual components of the assay are as follows:

Anti-microbial product antibody. The antibody against the microbial product is preferably of the IgM class. IgM-analyte immunocomplexes trigger a reaction sequence which results in the stimulation of white blood cell oxidant production via complement pathway activation. The antibody against the microbial product can also be of the IgG class. IgG binds to the Fc receptors on white blood cells and can cause reduction of the observed chemiluminescence. Under these circumstances, there is a decrease in the level of white blood cell activation from the normal level. This then also provides a semi-quantitative measure of the level of antigen present and shows an especially dramatic drop in white blood cell activation with high levels of antigen or mediator.

White Blood Cell Stimulant. Although zymosan or latex beads are preferred but not required as additions to the test procedure for the quantitation of microbial products, as described in copending and concurrently filed application Ser. No. 08/991,230, the inclusion of the stimulatory agent is necessary for the assessments of TNF response reserve, CLmax, and responsiveness to immunocomplexes (see below); thus it is included in all of the assays. Furthermore, chemiluminescence produced by immunocomplexes in the test sample is enhanced by inclusion of the agent. Zymosan and latex beads enhance the chemiluminescent response by stimulating concerted white cell oxidant production and phagocytosis. This stimulation can be further enhanced if the zymosan or latex beads are opsonized, through the binding of immunoglobulin G and complement factors (iC3b and C3b).

Chemiluminescent indicator. The phenomenon of chemiluminescence resulting from the production of neutrophil oxidants is described by Allen, R. C. *Methods in Enzymology* 133:449 (1986) using the acyl azide dye luminol as a light emitting agent. This technique permits the sensitive measurement of neutrophil respiratory burst activation using small numbers of polymorphonuclear leukocytes in whole blood. Other chemiluminescent dyes which produce light as a result of neutrophil oxidant production have also been identified including lucigenin and pholasin; others will be known by the skilled artisan.

Immunocomplexes to maximally stimulate white blood cells. Inclusion of a measure of the maximal response of the white blood cells in the patient sample to a maximal stimulatory level of immunocomplexes makes it possible to achieve quantitative results in accordance with this invention. This measure may be achieved with any antigen and corresponding anti-antigen antibody that achieves the desired stimulation, such as endotoxin (LPS) and anti-endotoxin (anti-LPS) antibody. Antibodies of the IgM class are preferred.

Assay procedure. In a typical example of the practice of the assessment, a sample of a suspected sepsis patient's whole blood may be tested for the level of gram-negative endotoxin. The blood sample is divided into two pairs of identical aliquots. One pair is used to measure the chemiluminescent response to immunocomplexes formed from any endotoxin present in the sample with added anti-endotoxin antibody; the second pair is used to obtain the overall chemiluminescent response to a maximal concentration of immunocomplexes. The first aliquot of whole blood is mixed with an antibody to endotoxin, preferably with a monoclonal antibody such as Xomen-E5(R), a murine monoclonal IgM pentamer directed against a lipid A component of gram-negative endotoxin, produced by Xoma, Palo Alto, Calif. In parallel, the second aliquot is used as a control, without added anti-endotoxin antibody. To measure maximal response with the second pair of blood sample aliquots, to one is added a maximally stimulatory dose of endotoxin and anti-endotoxin antibody. A control for this sample is prepared containing the added antigen but not the antibody. To all four of the thus-prepared aliquots is added luminol solution and complement-activated zymosan or complement-opsonized latex beads. The endotoxin level in the patient sample is determined from the ratio of the integrated differences in light emission by the pairs of aliquots (the "response factor") and a predetermined relationship between response factor and endotoxin level.

The chemiluminescent light emission may be measured in all four reaction aliquots for from about 10 minutes to about one hour. The preferred period is 10 to 20 minutes. After this period, the neutrophils appear to be progressively deactivated or spent with the result that the chemiluminescent response is appreciably decreased and is finally exhausted.

In the preferred embodiment of this invention, there is utilized a small volume of undiluted whole blood (10 $\mu$l to 50 $\mu$l), heparinized (<2 U/ml) or EDTA anticoagulated, and kept at room temperature. A blood sample is incubated with anti-endotoxin antibody at 37° C. for five to ten minutes. To determine the response factor, to one sample of blood is added a maximally stimulating level of an antigen such as endotoxin (800 pg/ml) and corresponding anti-antigen (in this instance anti-endotoxin) antibody; to the control, only the antigen (endotoxin) is added. After incubation of all four samples, 300 $\mu$l of 150 $\mu$M luminol solution is added to all four samples followed by 20 $\mu$l of complement-opsonized zymosan, (2.5–3.0×10$^9$ particles ml). All four samples are placed in a thermostatted (37° C.) luminometer and the luminescence integrated over the test period.

Examples of the standard curves and formula for calculating the response factor are contained in Ser. No. 08/991, 230 and U.S. Pat. No. 5,804,370, incorporated herein by reference. Other methods and protocols may be modified and still remain within the scope of the invention.

II Maximum oxidant production of neutrophils as measured by CLmax As mentioned above, the preferred procedure for quantitating microbial products described above also provides additional information useful for determining the stage of sepsis. Maximum chemiluminescence (CLmax), calculated as maximum luminometer light emission, measured in counts per minute (cpm), of the control tube containing only blood sample plus oxidant production stimulant (curve A of example I, below), is an indication of the white blood cell's oxidative response to a stimulus (opsonized zymosan) (see example III for the method). The peak (in cpm) of the curve produced is proportional to the degree of oxidant production and the ability of the white blood cell to respond to programmed opsonic challenge.

For example, in early infection, the CLmax is usually less than $3 \times 10^6$ cpm. During the cytokinemic stage of sepsis, the CLmax may rise to greater than $3 \times 10^6$. When the patient is in the anergic stage, the CLmax will become higher (greater than $10^7$ cpm).

III. Responsiveness of the patient's neutrophils to immunocomplexes Responsiveness, a measure of the maximal ability of the white blood cell to bind and respond to opsonized immunocomplexes, is calculated from the integrated chemiluminescence of two of the four aliquots described in the above method for quantitating microbial products in the patient's blood sample. Responsiveness is measured using the formula 1-(∫(aliquot containing exogenously-added antigen)/∫(aliquot containing exogenous antigen plus anti-antigen antibody)). A large responsiveness is indicative of a large response reserve for processing opsonized immunocomplexes and is viewed as the normal healthy state. A small responsiveness represents a diminished reserve for processing opsonized immunocomplexes and is indicative of an immunocompromised or diseased state (see FIG. 1).

For example during the early infection phase of sepsis, the responsiveness may be greater than 45%. During the cytokinemic phase, it may drop below 45%, and in the anergic phase, to less than 20%.

IV. Tumor necrosis factor (TNF) response reserve on neutrophils In order to access whether neutrophils have been activated by TNF the inventors have devised a TNF challenge assay. The principle of this assay is based on the premise that neutrophils which have not been exposed to TNF are able to be primed by a maximally priming exogenous dose of TNF to augment their oxidative burst capacity. Previous studies have shown that exposure of neutrophils to TNF results in a dose dependent priming of respiratory capacity which occurs rapidly (within 10 min. of exposure to this cytokine). Neutrophils have TNF receptors which are known to be shed into the circulation following exposure of the cells to TNF. If neutrophils are in the milieu of this cytokine at levels often associated with severe sepsis (>100 pg/ml), then they are unable to be further primed by this cytokine either as a consequence of maximal priming or loss of TNF receptors. Our studies have shown that this response to TNF is independent of other priming agents such as C5a. A maximal priming dose of C5a (10 pmole per assay) which is known to cause maximal extrusion of cryptic CR1 and CR3 receptors does not prevent further augmentation of oxidative capacity by a maximal riming dose of TNF (60 U/assay). These studies concur with the notion that the mechanism of TNF priming of oxidative burst in neutrophils includes mechanisms other than increased opsonin receptor expression. Signal transduction studies in neutrophils activated by various priming agents have shown that priming by C5a involves a "serpentine" (7 transmembrane domain) G protein linked membrane receptor which results in increases in intracellular calcium in neutrophils with subsequent activation of serine/threonine kinases such as protein kinase C. In contrast priming by TNF involves a single transmembrane domain receptor which activates a tyrosine kinase signal transduction pathway. The TNF challenge assay is executed in a manner analogous to the endotoxin assay using identical reagents excluding anti-LPS antibodies. The assay contains a maximal stimulatory dose of TNF (60 U/tube) and the control tube identical to that used in the microbial products assay, which contains only the blood sample plus stimulant. The TNF response reserve is calculated as:
1-{[control 20 min. light integral]/[maximal TNF stimulation 20 min. light integral]}. A low reserve indicates that the patients neutrophils are already near maximally primed by prior exposure to endogenous TNF. A high reserve implies that the neutrophils are "naive" to TNF and hence capable of significant increases in priming (see FIG. 3).

For example, during the early infection stage of sepsis, the TNF receptor reserve may be greater than 40%. During the cytokinemic phase, this value may decrease to less than 20%. During the anergy stage, the value may be variable.

The following examples will serve to illustrate the invention.

MATERIALS AND METHODS

Reagents and bacterial products. Luminol (5-amino-2,3-dihydro-1,4-phthalazinedione, free acid), zymosan A (*Saccharomyces cerevisiae*), lipopolysaccharides from *Escherichia coli* (*E. coli*) serotypes (026:B6, 055:B5, 0111 :B4) (gram-negative endotoxin), and lipoteichoic acids from Streptococcus spp. (Gram-positive endotoxin) were purchased from Sigma (Sigma Chemical Co., St. Louis, Mo.), tumor necrosis factor from (R&D Systems, Minneapolis Minn.).

Chemiluminescence Reagents. Buffer for measurement of whole blood or white cell chemiluminescence studies was HBSS (pyrogen free, endotoxin less than 0.005 EU/ml) containing 1.5 mM calcium salt and 0.9 mM magnesium salt (Gibco BRL, Grand Island, N.Y.). This buffer (500 ml) was vigorously mixed overnight at 25° C. with luminol to yield a saturated solution (150 M, HBSS-luminol) and then supplemented with 4 U/ml of lithium heparin.

Opsonized Zymosan. To prepare human complement-opsonized zymosan, pooled fresh frozen citrate anti-coagulated human plasma was dialyzed against 4 volumes of 28.5% saturated ammonium sulfate solution for 2 hours at room temperature and then against fresh 28.5% saturated ammonium sulfate overnight at 4° C. The precipitate was removed by centrifugation and the supernatant dialyzed against 2 changes of 10 volumes of HBSS without calcium and magnesium at 4° C. This immunoglobulin-depleted serum fraction (<10% IgG and IgM based on nephelometric assay) was then mixed with a half volume of heat-activated zymosan A (5 g/liter of normal saline) in the presence of 1.3 mM calcium salt and 0.9 mM magnesium salt for 15 minutes at room temperature to opsonize the zymosan. The opsonized zymosan was subsequently washed three times with 2 volumes of ice-cold sterile normal saline and resuspended in its original volume (approx. $3 \times 10_6$ particles per microliter).

Chemiluminescent Assays. All glass surfaces used for microbial product assays or storage of reagents for microbial product assay including assay tubes were depyrogenated by heating to 300° C. for at least 6 hours. All polystyrene and polyethylene surfaces used for storage of antibodies, HBSS-luminol or blood products were sterile and essentially endotoxin free as determined by chromogenic LAL assay of pyrogen free water left in contact with the surface of interest. All pipette tips used for fluid transfer were sterile and pyrogen free (Diamed, Mississauga, Ontario, Canada). Blood samples used for the assay were drawn by venipuncture or through indwelling arterial lines into sterile 3 ml EDTA anti-coagulated Vacutainer tubes (Becton Dickenson, Franklin Lakes, N.J.) which were pretested for LPS content (less than 0.005 EU/ml).

All chemiluminescence experiments utilizing whole blood or cell fractions were assayed in triplicate and the results expressed as the mean luminometer counts per minute ±1 SD. In all assays. HBSS-luminol buffer (300 ul) was pre-mixed with 30 ul of antibody solution and subsequently incubated with 10 ul of whole blood or isolated neutrophils in fresh human plasma. After incubation with blood at 37° C. for 5 minutes in a thermostatted aluminum heating block the assay tubes were transferred to the chemiluminometer (E. G. & G. Berthold Autolumat LB953, Wildbad, Germany) for addition of 20 ul of human complement-opsonized zymosan. All assays were incubated at 37° C. in the chemiluminometer for 20 minutes with continuous measurement of light emission from each tube at least every 60 seconds for a minimum 0.6 second counting window. Chemiluminescence reaction curves and integrals were captured using Axis Cellular Luminescence System Software (version 1.03 from ExOxEmis Inc., San Antonio, Tex.).

Example I
Quantitation of Endotoxin (Lipopolysaccharide, LPS)

To permit quantitation of endotoxin in whole blood, the following reaction aliquots were set up:

A=Whole blood+opsonized zymosan

B=Whole blood+anti-LPS antibody+opsonized zymosan

C=Whole blood+exogenous LPS (800 pg/ml)+opsonized zymosan

D=Whole blood+exogenous LPS (800 pg/ml)+opsonized zymosan+anti-LPS antibody.

All reaction aliquots contained opsonized zymosan in order to optimize oxidant production of the patient's white blood cells in response to immunocomplexes. In addition to the patient's blood sample and zymosan, tube B contained antibody against the microbial product to be measured, in this case endotoxin. Tube A served as a control to tube B. In order to determine the maximal response of the patient's white blood cells to immunocomplexes, tube C contained the maximal stimulatory concentration of LPS from *E. coli* 055:B5 plus anti-endotoxin antibody (determined to be 800 pg/ml or 0.67 EU/ml at an antibody concentration of 0.8 ug/assay); control tube D contained the same amount of antigen but no antibody. While in this example the antigen used to form immunocomplexes to determine maximal response (endotoxin-anti-endotoxin) was identical to the microbial product analyte, this does not need to be the case. The response factor, $RF=\int(B-A)/\int(D-C)$, was calculated as the difference between the antibody-dependent (tube B) and non-antibody-dependent (tube A) twenty-minute reaction integrals divided by the difference in antibody-dependent (tube D) and non-antibody-dependent (tube C) twenty-minute reaction integrals of reaction mixtures containing a maximal stimulatory dose of endotoxin.

As described in copending and concurrently filed application Ser. No. 08/991,230, a sharp dose-response curve of the response factor was achieved between 0 and 80 pg/ml endotoxin, then a more gradual response was seen over a range of 80 to 800 pg/ml (0.67–1.6 EU/ml) with a plateau value between 800 and 2000 pg/ml. From the value of the response factor from a patient's blood, the endotoxin level can be interpolated.

Example II
CLmax and Responsiveness as Staging Indices in Septic Patients:

As mentioned above, this procedure for quantitating microbial products also provides additional information useful for determining the stage of sepsis. Maximum chemiluminescence ($CL_{max}$), calculated as maximum luminometer light emission, measured in cpm, of curve A, is an indication of the white blood cell's oxidative response to a stimulus (opsonized zymosan). The peak (in cpm) of the curve produced is proportional to the degree of oxidant production and the ability of the white blood cell to respond to programmed opsonic challenge. CLMAX is therefore a measure of both white blood cell concentration and activation state.

Responsiveness, a measure of the maximal ability of the white blood cell to bind and respond to opsonized immune complexes, is calculated from the same procedure using the formula 1-C/D. A large responsiveness is indicative of a large response reserve for processing opsonized immunocomplexes and is viewed as the normal healthy state. A small responsiveness represents a diminished reserve for processing opsonized immunocomplexes and is indicative of an immunocompromised or diseased state.

Figure 1:
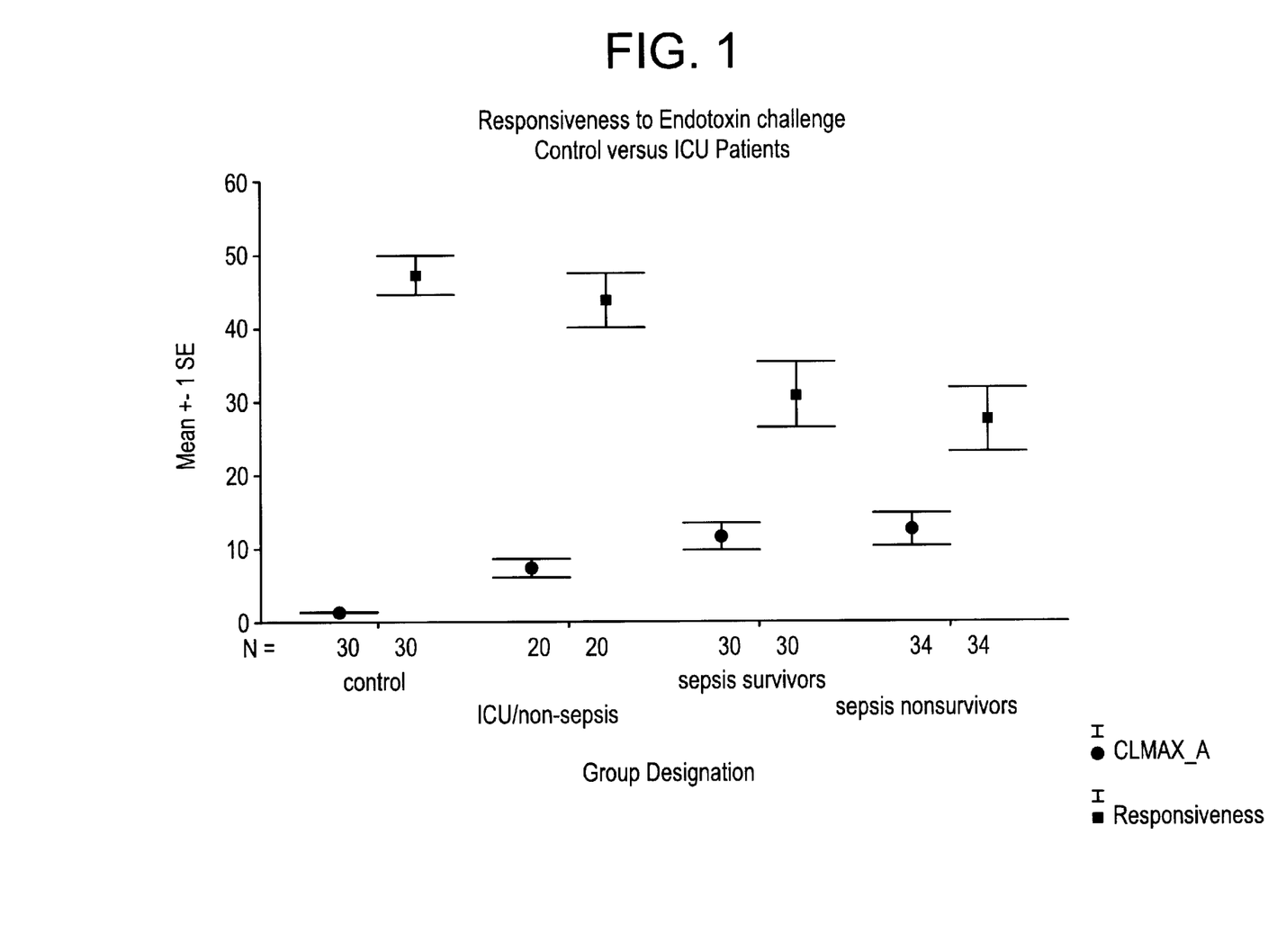
FIG. 1 compares the responsiveness and CLmax values for neutrophils from patients in the following groups: control patients, intensive care unit (ICU) patients found to be non-sepsis, survivors from sepsis, and non-survivors of sepsis.
Figure 2:
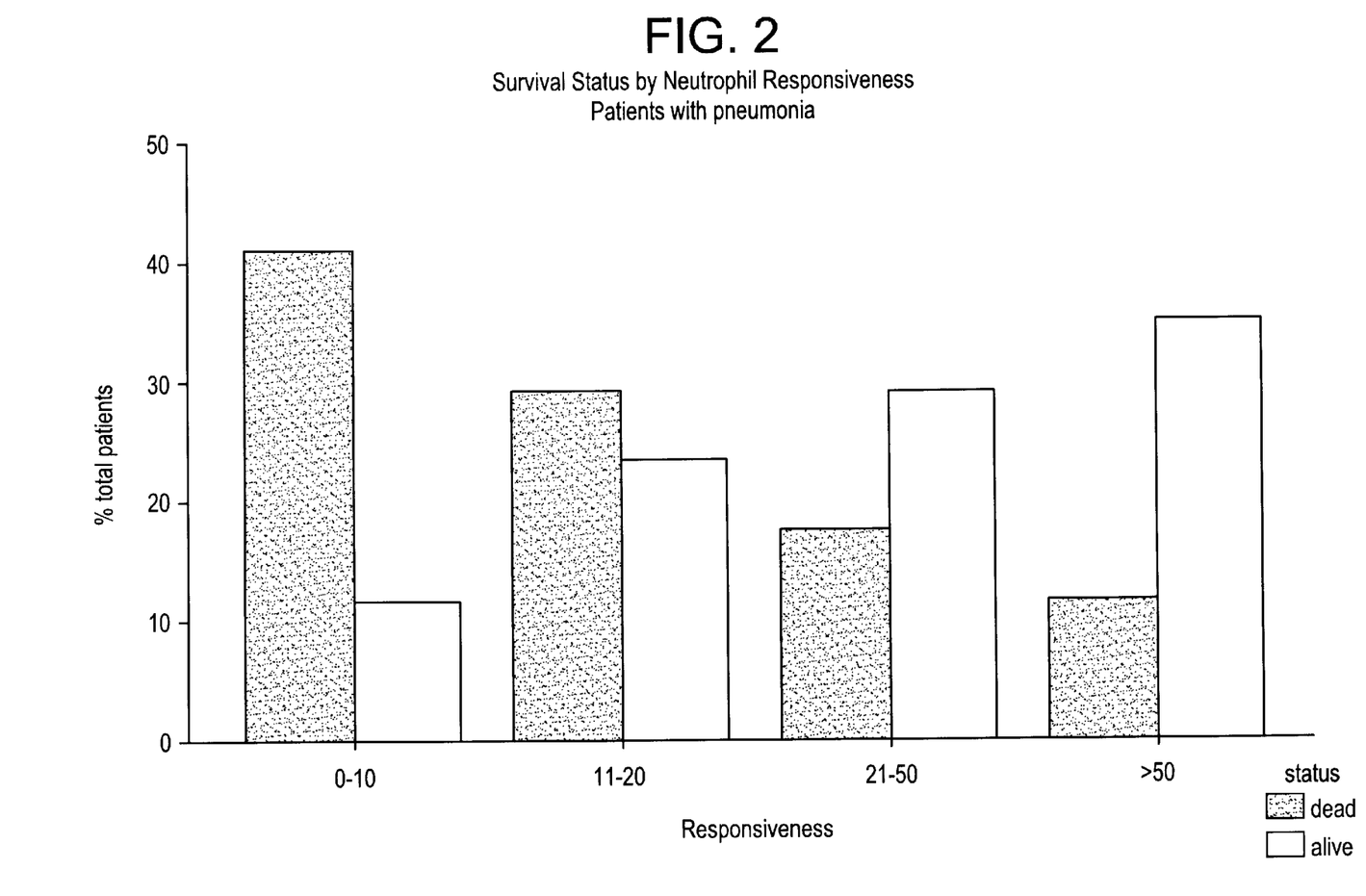
FIG. 2 depicts the relationship between the level of neutrophil responsiveness, in percentile ranges, and the mortality outcome in patients with pneumonia.

The chemiluminescent assay procedure as described in Example I was performed on a large number of blood samples from various control individuals and hospitalized patients. In FIG. 1 a comparison is made of Responsiveness (squares) and CLMAX (circles) values in various patient populations. In the three ICU groups shown (intensive care unit (ICU)/non sepsis, sepsis survivors and sepsis non-survivors), patients were evaluated at the time of admission to the intensive care unit. This figure shows the progressive increase in CLMAX as the patient populations become more acutely ill, due to a combination of increased neutrophil priming and overall cell number. This increase in neutrophil activation most likely reflects an increase in the systemic levels of pro-inflammatory mediators such a Platelet Activating Factor (PAF), cytokines (TNF and IL.1), complement activation products (C5a), leukotrienes (LTB4) and possibly bacterial, viral or fungal products. The figure also shows a progressive decline in Responsiveness with increased disease severity. This effect is attributed to an exhaustion of the humoral complement opsonizing and/or neutrophil activation capacity to respond to an immune complex challenge. In a clinical trial involving sepsis patients with pneumonia (n=53), we found that a correlation existed between mean Responsiveness (measured on admission to the unit or upon presentation with SIRS criteria) and mortality outcome (logistic regression analysis, p<0.03). As shown in FIG. 2, patients who succumbed to pneumonia had a lower mean Responsiveness (19.4%) than those who survived (mean Responsiveness 35.5%).

Example III
Determination of TNF Response Reserve by TNF Challenge Assay

Figure 3A:
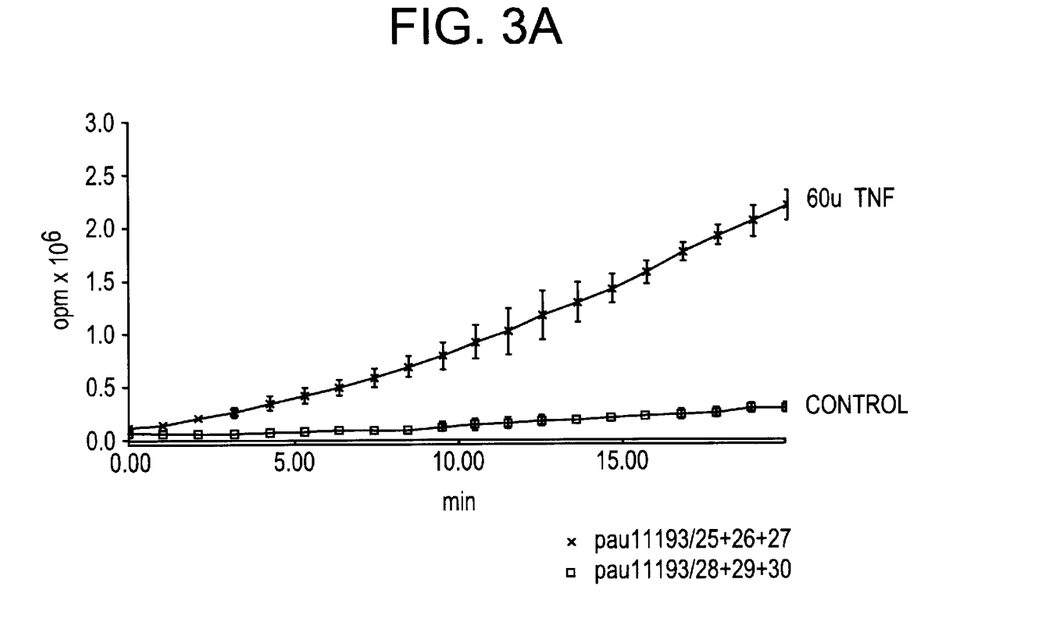
FIG. 3 shows the chemiluminescent response of neutrophils with an added maximum stimulatory dose of tumor necrosis factor, from a patient with a high level of TNF response reserve (above) and a patient with no response reserve (below).
Figure 3B:
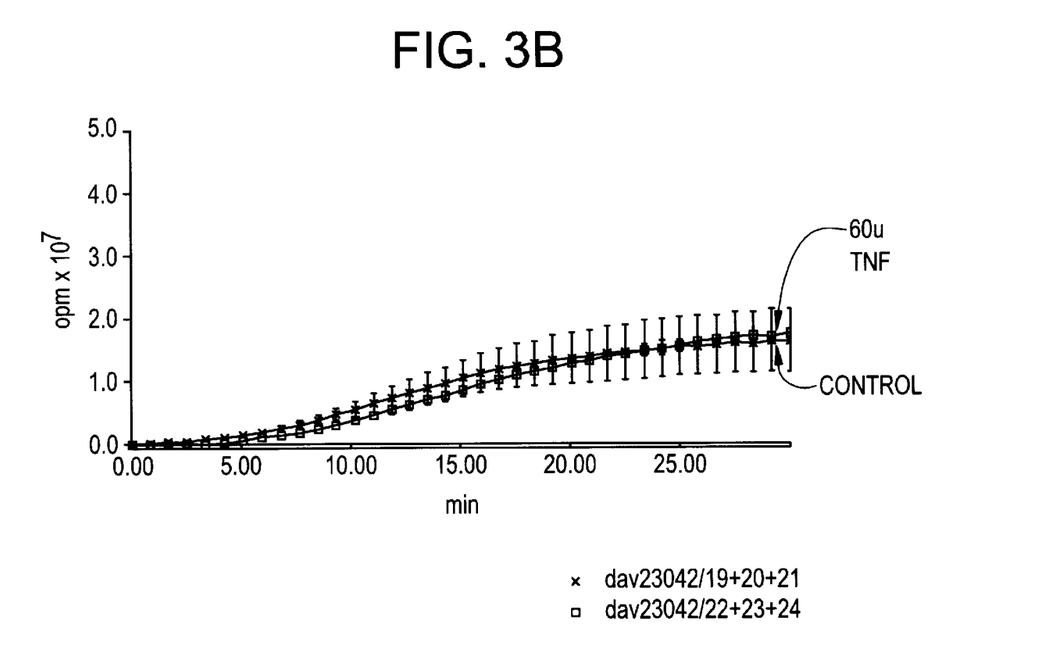

Tumor necrosis factor (TNF) response reserve of patient's neutrophils was evaluated using the chemiluminescence procedure similar to that described in the examples above. An additional aliquot of the patient's blood sample was combined with a maximal stimulatory dose of TNF, predetermined to be 60 units. The control sample was that of aliquot A of the preceding example. The chemiluminescence reaction was triggered by the addition of 20 ul of human complement opsonized zymosan. The luminescence signal is integrated for 20 min. at 37 degrees C. FIG. 3 shows the results of a TNF challenge assay on a patient with a large reserve of TNF response (upper panel), and a patient with no response reserve (lower panel). The TNF challenge assay is therefore used to measure the TNF response reserve of neutrophils as described above.

In order to validate the TNF challenge assay and the TNF response reserve index a series of longitudinal patient studies were conducted. Because TNF is difficult to measure reproducibly in septic patients due to the simultaneous presence of soluble TNF receptors which can interfere with many conventional ELISA assays and which precludes the detection of the "cytokinemic" phase of sepsis, IL-6 was measured as a cytokine indicator of the cytokinemic phase of sepsis. IL-6 appears in the circulation approximately 6–8 hours following the peak in TNF release and is a more reliable indicator of pro-inflammatory cytokine activation. The following results summarized in Table 5 were obtained on three septic patients using serial assays: (IL-6 is normally not detectable in the absence of infection or acute phase response).

| Patient No. | Study Day | LPS pg/ml | TNF response reserve | IL-6 pg/ml | Outcome |
|---|---|---|---|---|---|
| 1 | 1 | 120 | 74 | 105 | Patient died |
|   | 2 | 35 | 62 | 0 |  |
|   | 4 | 150 | 20 | 1600 |  |
| 2 | 1 | 30 | 66 | 0 | Patient died |
|   | 2 | 400 | 67 | 0 |  |
|   | 3 | not detected | 2 | 175 |  |
| 3 | 1 | 300 | 0 | 180 | Patient survived |
|   | 2 | 250 | 20 | 0 |  |
|   | 3 | 60 | 40 | 0 |  |

Most normal individuals have TNF response reserves of 40% or greater based on our study of 15 normal healthy ambulatory controls. The results in the above table highlight several important features of the TNF challenge assay and TNF response reserve as a measure of neutrophil exposure to cytokine-dependent neutrophil activators such as TNF. In each patient the decline in TNF response reserve was associated with an elevation in IL-6, indicative of activation of the pro-inflammatory cytokine cascade. A depression or persistent decline in TNF response reserve was often associated with prior exposure to LPS and an increased risk of mortality.

Example IV
Clinical Utility of the Chemiluminescence Assays

To validate the utility of whole blood chemiluminescence for quantitating endotoxin, evaluating neutrophil immunoresponsiveness, and determining the association between endotoxemia and clinically important outcomes for critically ill patients, whole blood measurements were made on 74 consecutive patients upon admission to the Medical Surgical Intensive Care Unit. One hundred and one patients who met sepsis criteria as defined by ACCP/SCCM consensus were prospectively studied. Daily assays in quadruplicate were obtained.

Results of the quantitative LPS assay, maximum chemiluminescence, and responsiveness of patients categorized in this way are presented in the following table:

| Category | N | LPS (pg/ml) | CLMAX | responsiveness |
|---|---|---|---|---|
| control | 30 | — | 1.2 ± 0.8 | 47.1 ± 15 |
| non-sepsis | 20 | 226 ± 345 | 7.1 ± 5.6* | 43.5 ± 17 |
| sepsis | 64 | 404 ± 354# | 12.0 ± 11.8*^ | 29.0 ± 24* |

*$p = 0.0001$ vs. control; ^$p = 0.001$ vs. non-sepsis; #$p = 0.05$

It is apparent from these data that CLMAX and Responsiveness to endotoxin can be used to differentiate septic from non-septic patients. They provide a measure of the cumulative effect of pro-inflammatory and anti-inflammatory cytokines on the neutrophil.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method of determining the stage of sepsis of a patient from a sample of patient's blood, said sample comprising plasma and white blood cells, said method comprising the concurrent measurement of:
   (i) the level of microbial products;
   (ii) the tumor necrosis factor response reserve on the patient's neutrophils;
   (iii) the maximum oxidant production by the patient's neutrophils; and
   (iv) the level of responsiveness of the patient's neutrophils to a maximum stimulatory level of immunocomplexes;
and correlating the results to effect the desired determination.

2. The method of claim 1 wherein the microbial products are selected from the group consisting of gram-positive bacteria, gram-negative bacteria, fungi, viruses, gram-positive cell wall constituents, lipoteichoic acid, peptidoglycan, teichoic acid, gram-negative endotoxin, lipid A, and combinations thereof.

3. The method of claim 1 sequentially comprising:
   i) providing five aliquots of equal volume of said sample, indicated as aliquots A, B, C, D and E;
   ii) providing aliquot B with an amount of anti-microbial product antibody sufficient to form an immunocomplex with said microbial product in the sample, to provide reaction aliquot B;
   iii) providing aliquot A as a control to reaction aliquot B without said anti-microbial product antibody, to provide reaction aliquot A;
   iv) providing aliquot D with a maximal stimulatory amount of antigen, together with an amount of anti-antigen antibody sufficient to form an immunocomplex with said antibody, to provide reaction aliquot D;
   v) providing aliquot C, as a control to reaction aliquot D, with an amount of antigen equal to that provided in reaction aliquot D, but without said anti-antigen antibody, to provide reaction aliquot C;
   vi) providing aliquot E with a maximum stimulating dose of tumor necrosis factor;
   vii) contacting an agent capable of stimulating oxidant production by white blood cells to reaction aliquots A, B, C, D, and E;
   viii) incubating reaction aliquots A, B, C, D and E for a time sufficient for any immunocomplexes present and formed in reaction aliquots A, B, C, or D to react with the white blood cells and complement proteins in the plasma to produce oxidants, and for the tumor necrosis factor in reaction aliquot E to maximally prime white blood cells to produce oxidants;
   ix) contacting a chemiluminescent compound which reacts with said oxidants to generate light with reaction aliquots A, B, C, D and E, prior to or after step vii);
   x) measuring light emission from reaction aliquots A, B, C, D and E over a predetermined time period; and
   xi) correlating differences in light emission among reaction aliquots A, B, C, D and E to indicate:
      a) the level of microbial products calculated from the preestablished relationship which correlates response factor to microbial product level, said response factor determined from said light emissions from said reaction aliquots A, B, C, D using the formula $\int(B-A)/\int(D-C)$;

b) the tumor necrosis factor response reserve on the patient's neutrophils determined using the formula $1-[\int A/\int E]$;

c) the maximum oxidant production by the patient's neutrophils determined as the value A; and d) the level of responsiveness of the patient's neutrophils to a stimulatory level of immunocomplexes, determined from the formula $1-(\int C/\int D)$.

4. The method of claim 3 wherein the agent capable of increasing oxidant production by white blood cells on exposure to immunocomplexes or tumor necrosis factor is selected from the group consisting of zymosan, latex particles, opsonized zymosan, opsonized latex particles, and combinations thereof.

5. The method of claim 3 wherein said chemiluminescent compound is selected from the group consisting of luminol, lucigenin and pholasin.

6. The method of claim 3 wherein said anti-antigen antibody and said antigen are anti-lipopolysaccharide antibodies and lipopolysaccharide, respectively.

7. The method of claim 3 wherein said anti-microbial product antibody is a monoclonal antibody of class IgM or IgG.

8. The method of claim 3 wherein said microbial product is selected from the group consisting of gram-positive bacteria, gram-negative bacteria, fungi, viruses, gram-positive cell wall constituents, [such as] lipoteichoic acid, peptidoglycan, teichoic acid, gram-negative endotoxin, lipid A, and combinations thereof.

9. A diagnostic kit for determining the stage of sepsis from a sample of patient's blood comprising:

i) a first container of IgM or IgG antibody specific to a microbial product;

ii) a second container of chemiluminescent compound;

iii) a third container of antigen;

iv) a fourth container of anti-antigen antibodies;

v) a fifth container of tumor necrosis factor; and vi) a sixth container of an agent capable of increasing oxidant production by white blood cells on exposure to immunocomplexes or tumor necrosis factor.

10. The diagnostic kit of claim 9 wherein said microbial product is selected from the group consisting of gram-positive bacteria, gram-negative bacteria, fungi, viruses, gram-positive cell wall constituents, lipoteichoic acid, peptidoglycan, teichoic acid, gram-negative endotoxin, lipid A, and combinations thereof.

11. The diagnostic kit of claim 9 wherein the agent capable of increasing oxidant production by white blood cells on exposure to immunocomplexes or tumor necrosis factor is selected from the group consisting of zymosan, latex particles, opsonized zymosan, opsonized latex particles, and combinations thereof.

* * * * *